US00PP14422P29

(12) United States Plant Patent

Olesen et al.

(10) Patent No.: US PP14,422 P2
(45) Date of Patent: Dec. 30, 2003

(54) SHRUB ROSE PLANT NAMED 'POULOESY'

(50) Latin Name: *Rosa hybrida*
Varietal Denomination: POULoesy

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 116 days.

(21) Appl. No.: 09/676,601

(22) Filed: Sep. 27, 2000

(51) Int. Cl.[7] ..... A01H 5/00
(52) U.S. Cl. ..... Plt./107
(58) Field of Search ..... Plt./107

(56) References Cited

U.S. PATENT DOCUMENTS

PP6,281 P * 9/1988 Meilland ..... Plt./107

OTHER PUBLICATIONS

Community Plant Variety Office. "Certificate on the Grant of Community Plant Variety Rights" Nov. 6, 2000 6 pages EU.

UPOV–ROM GTITM Computer Database, GTI JOUVE Retrieval Software, 2001/02, citations for 'POULoesy'.*

* cited by examiner

*Primary Examiner*—Bruce R. Campell
*Assistant Examiner*—W C Haas

(57) ABSTRACT

A new shrub rose plant which has abundant flowers and attractive foliage. The plant has strong even growth and a free branching habit. This new and distinct variety has shown to be uniform and stable in the resulting generations from asexual propagation.

1 Drawing Sheet

SUMMARY OF THE INVENTION

The present invention constitutes a new and distinct variety of shrub rose plant which originated from a controlled crossing between an unnamed seedling and 'La Sevillana' (U.S. Plant Pat. No. 6,384, issued on Nov. 8, 1988). The two parents were crossed and the resulting seeds were planted in a controlled environment. The new variety is named 'POULoesy'.

The objective of the hybridization of this rose variety for commercial culture was to create a new and distinct variety with unique qualities, such as:

1. Uniform and abundant flowers;
2. Strong even growth with a free branching habit;
3. Flowers with a light rose scent.
4. Glossy and disease resistant foliage which requires limited maintenance, making it ideal for use in landscapes.

The combination of qualities of this variety represents significant improvement over previously available commercial cultivars of this type and distinguishes 'POULoesy' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULoesy' was selected by the inventors as a single plant from the progeny of the hybridization in Fredensborg, Denmark, in May of 1991. Asexual reproduction of 'POULoesy' by cuttings and tradtional budding was first done by L. Pernille and Mogens N. Olesen in Fredensborg, Denmark in August of 1991. This initial and other subsequent propagations conducted in controlled environments have demonstrated that the characteristics of 'POULoesy' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULoesy'. Specifically illustrated in the drawing:

1. Stem showing branches and the attachment of leaves, buds, and peduncles;
2. Flower bud, partially opened bud, and open bloom;
3. Flower petals, detached;
4. Sepals, receptacle, and pedicel;
5. A bare stem exhibiting thorns;
6. Leaves.

DETAILED DESCRIPTION OF THE VARIETY

The following is a description of 'POULoesy', as observed in its growth in a nursery in Jackson County, Oreg., on plants aged one year. Color references are made using The Royal Horticultural Society (London, England) Colour Chart, 1995, except where common terms of color are used.

For a comparison, several physical characteristics of the rose variety 'POULrijk', a shrub rose variety from the same inventors described and illustrated in U.S. Plant Pat. No. 12,519, are compared to 'POULoesy' in Chart 1.

CHART 1

| | 'POULoesy' | 'POULrijk' |
|---|---|---|
| Bud Color at ¼ Open | Red Group 47C/D. | Red Group 53C. |
| Upon opening, color of upper surface of petal | Outermost Petals: Red Group 43B. Innermost Petals: Red Group 52A. | Outermost Petals: Red Group 53A/B. Innermost Petals: Red Group 53A/B. |
| Basal petal spot, upper surface of petal | Outermost Petals: Green-White Group 157C. | Outermost petals: Green-White Group 157D Innermost Petals: Green-White Group 157D. |

Parents: Unnamed seedling (seed parent)×La Sevillana (pollen parent).

Classification:

*Botanical.*—*Rosa hybrida.*

*Commercial.*—Shrub.

FLOWER AND FLOWER BUD

Blooming habit: Continuous.

Flower bud:

*Size.*—Upon opening, 19 mm–22 mm in length from base of receptacle to end of bud.

*Bud form.*—Long, pointed ovoid.

*Bud color.*—As sepals unfold, Red Group 47B; Red Group 47C/D at ¼ opening.

*Sepals.*—Yellow-Green Group 146A/B. Weak foliaceous appendages on three of the five sepals. Surfaces of sepals somewhat rough with limited pubescence. Stipitate glands are present in moderate quantities on edges of sepals.

*Receptacle.*—Surface: Smooth. Shape: Pear-shaped. Size: 8 mm (h)×7 mm (w). Color: Yellow-Green Group 144A.

*Peduncle.*—Surface: Smooth with limited quantities of stipitate glands. Length: 22 to 27 mm average length. Color: Yellow-Green Group 144B. Strength: Upright.

*Borne.*—Generally with 15 to 20 buds per flowering stem.

Flower bloom:

*Fragrance.*—Light.

*Duration.*—As a cut flower 2 to 3 days. The blooms have a duration on the plant of 6 to 7 days.

*Size.*—Medium. Average flower diameter is 70 mm when open.

*Form.*—Shape of flower when viewed from the side: Upon opening, upper part: Flattened convex. Upon opening, lower part: Flattened convex. Open flower, upper part: Flat. Open flower, lower part: Flattened convex.

*Petalage.*—Average range: 17 to 22 petals under normal conditions with 3 to 5 petaloids.

Color:

*Upon opening, petals.*—Outermost petals: Upper surface: Red Group 43B. Reverse side: Red Group 52A. Innermost petals: Upper surface: Red Group 43B. Reverse side: Red Group 52A.

*Upon opening, basal petal spots.*—Outermost petals: Outer side: Green-White Group 157C. Inner side: Green-White Group 157C. Innermost petals: Outer side: Green-White Group 157C. Inner side: Green-White Group 157C.

*After opening, petals.*—Outermost petals: Upper surface: Red Group 55C. Reverse side: In the margin, Red Group 52A; Red Group 55D in the middle zone. Innermost petals: Upper surface: Red Group 55C. Reverse side: In the margin, Red Group 52A; Red Group 55D in the middle zone.

*Upon opening, basal petal spots.*—Outermost petals: Outer side: Green-White Group 157C. Inner side: Green-White Group 157C. Innermost petals: Outer side: Green-White Group 157C. Inner side: Green-White Group 157C.

General tonality: On open flower, Red Group 52B. No change in the general tonality at the end of the 4th day. Afterwards, general tonality is Red Group 52C.

Petals:

*Petal reflex.*—Petals reflex slightly.

*Petal edge.*—Uniform.

*Shape.*—Deltoid.

*Petaloids.*—Present. Quantity: 3 to 5.

*Thickness.*—Average.

*Arrangement.*—Informal.

Reproductive organs:

*Pollen.*—Color: Yellow-Orange group 17A. Abundance: Limited.

*Anthers.*—Size: Small. Color: Greyed-Orange Group 165A. Quantity: 25 to 30.

*Filaments.*—Color: Yellow Group 2D.

*Stigmas.*—Slightly superior in location to anthers. Color: Greyed-Yellow Group 162D. Quantity: 20 to 25.

*Styles.*—Color: Green-White Group 157B/C.

*Hips.*—None observed.

PLANT

Plant growth: Very vigorous, upright to bushy. About 68 cm to about 89 cm in height at first season, grows to height of 107 to 124 cm. Plant is capable of obtaining a spread of about 122 cm.

Stems:

*Color.*—Young wood: Yellow-Green Group 144A with intonations of Greyed-Red Group 178A. Older wood: Yellow-Green Group 143C.

*Prickles.*—Incidence: Moderate. Size: Average length: 4 mm–5 mm. Color: Yellow-Green 145B; upper edge of prickle is Greyed-Red Group 181A. Shape: Linear to deeply concave.

*Surface.*—Young wood: Smooth. Older wood: Smooth.

Plant foliage: Normal number of leaflets on leaves in middle of the stem: 7 leaflets.

*Leaf size.*—60 mm (l)×40 mm (w).

*Quantity.*—Abundant.

*Color.*—Upper leaf surface: Green Group 137A. Lower leaf surface: Yellow-Green Group 146B. Juvenile foliage: Yellow-Green Group 146B. Anthocyanin intonation: Present on stipule, petiole, rachis, and prickles. Color is Greyed-Red Group 178A.

Plant leaves and leaflets:

*Stipules.*—Size: 23 mm–27 mm. Color: Yellow-Green Group 144B. Stipitate glands present in limited quantities on edge of stipules.

*Petiole.*—Length: 7 mm–10 mm. Color: Green Group 144A. Underneath: Green-Yellow Group 145A. With single prickle.-

*Rachis.*—Color: Yellow-Green Group 144B. Underneath: Yellow-Green Group 144A.

*Leaflet.*—Edge: Serrated. Shape: Acute. Other: Moderately glossy on upper surface; thick. Size: 25 mm (l)×18 mm(w).

Disease resistance: Above average resistance to mildew, rust, black spot, and Botrytis under normal growing conditions in Half Moon Bay, Calif.

We claim:

1. A new and distinct variety of rose plant of the Shrub class, substantially as herein illustrated and described as a distinct and novel landscape rose variety due to its abundant flowers, vigorous and compact growth, and low maintenence requirement.

* * * * *

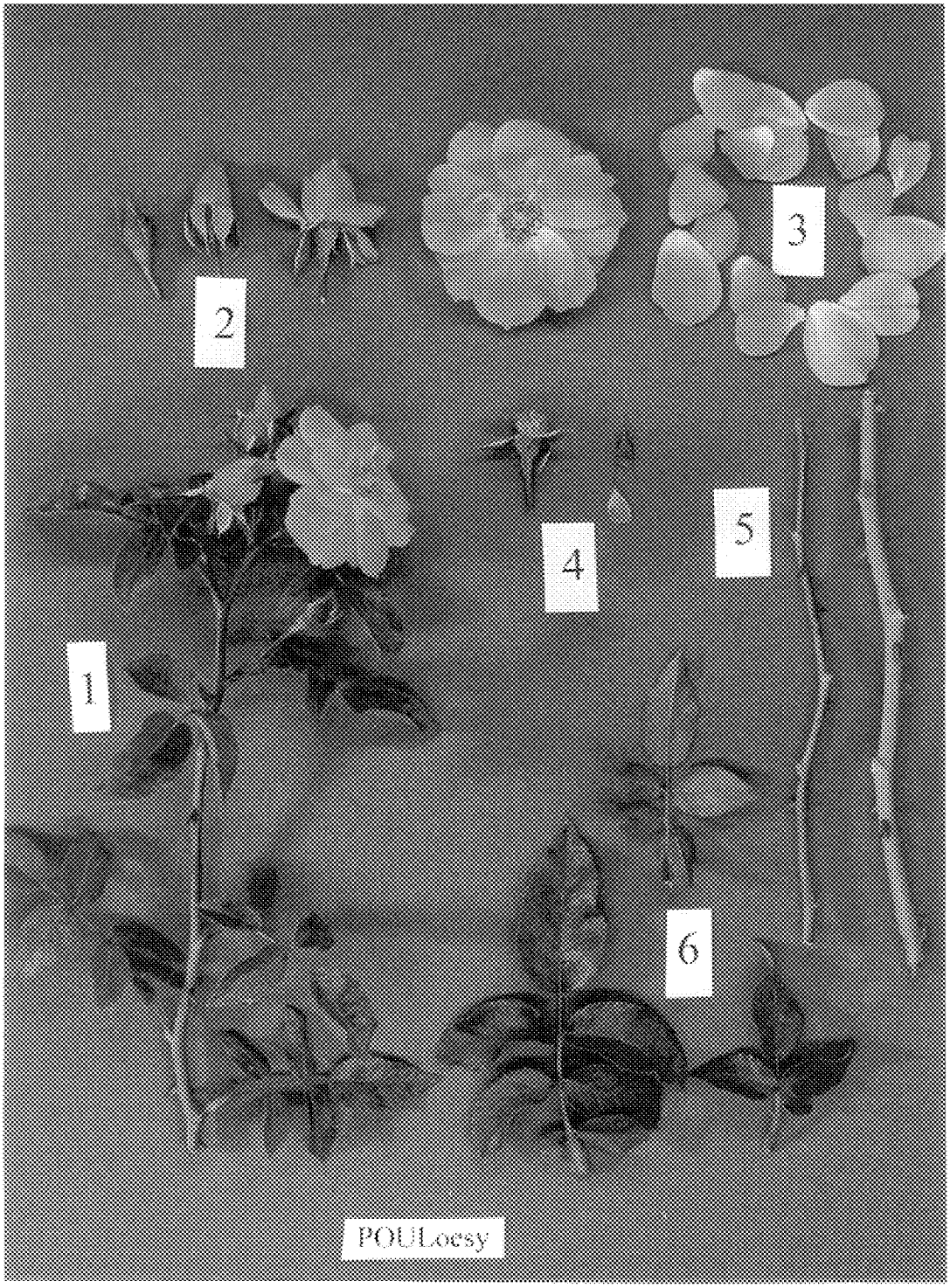
1
2
3
4
5
6
POULocsy